United States Patent [19]

Okuda et al.

[11] Patent Number: 4,618,495

[45] Date of Patent: Oct. 21, 1986

[54] PREPARATION FOR REDUCING CANCER SYMPTOMS WITHOUT TREATING CANCER

[75] Inventors: Hiromichi Okuda, Matsuyama; Hiroshi Masuno, Ehime; Masaki Aburada; Shigefumi Takeda, both of Kawasaki; Eiko Itoh, Nagareyama; Moe Matsushita, Machida; Eikichi Hosoya, Tokyo, all of Japan

[73] Assignee: Tsumura Juntendo Inc., Tokyo, Japan

[21] Appl. No.: 701,458

[22] Filed: Feb. 14, 1985

Related U.S. Application Data

[63] Continuation-in-part of Ser. No. 509,200, Jun. 29, 1983, abandoned.

[30] Foreign Application Priority Data

Aug. 25, 1982 [JP]   Japan .................................. 57-146143

[51] Int. Cl.⁴ .............................................. A61K 35/78
[52] U.S. Cl. .................................................. 424/195.1
[58] Field of Search ....................................... 424/195.1

[56] References Cited

U.S. PATENT DOCUMENTS

| 4,202,877 | 5/1980 | Sato et al. | 424/43 |
| 4,339,435 | 7/1982 | Adachi et al. | 424/115 |
| 4,419,349 | 12/1983 | Kojima et al. | 424/195.1 |

Primary Examiner—Jerome D. Goldberg
Assistant Examiner—John W. Rollins
Attorney, Agent, or Firm—Ladas & Parry

[57] ABSTRACT

A composition for reducing cancer symptoms by improving lipid metabolism and eliminating or reducing anorexia in tumor-bearing patients through inhibition of the lipid degradation-promoting action of toxohormone L which comprises an aqueous or aqueous organic solvent extract of one or more crude preparations selected from the group consisting of Astragali radix, Cinnamomi cortex, Rehmanniae radix, Paeoniae radix, Cnidii rhizoma, Atractylodis lanceae rhizoma, Angelicae radix, Ginseng radix, Hoelen and Glycyrrhizae radix, a method for preparing such a composition, and a method for reducing cancer symptoms using the composition.

4 Claims, 5 Drawing Figures

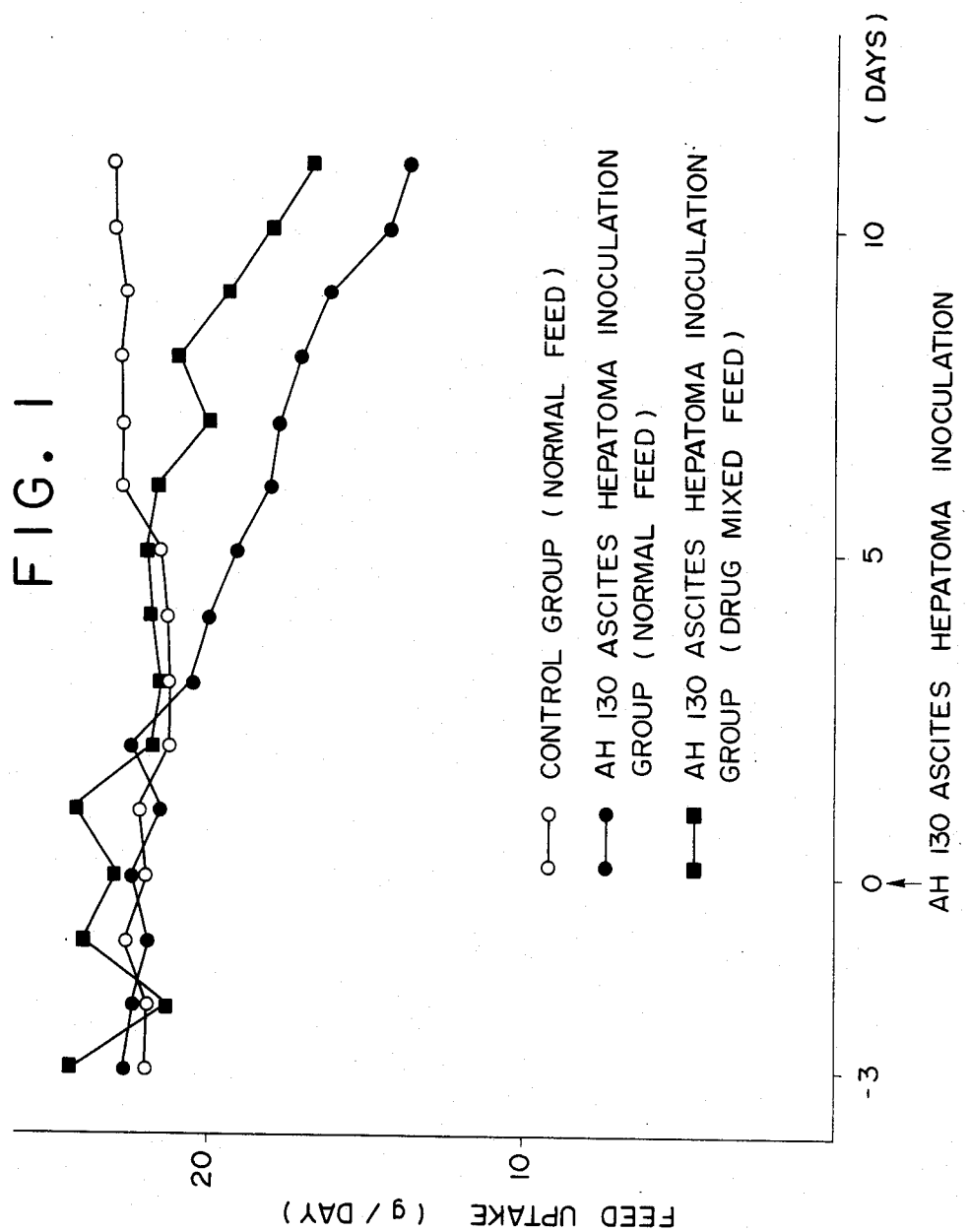

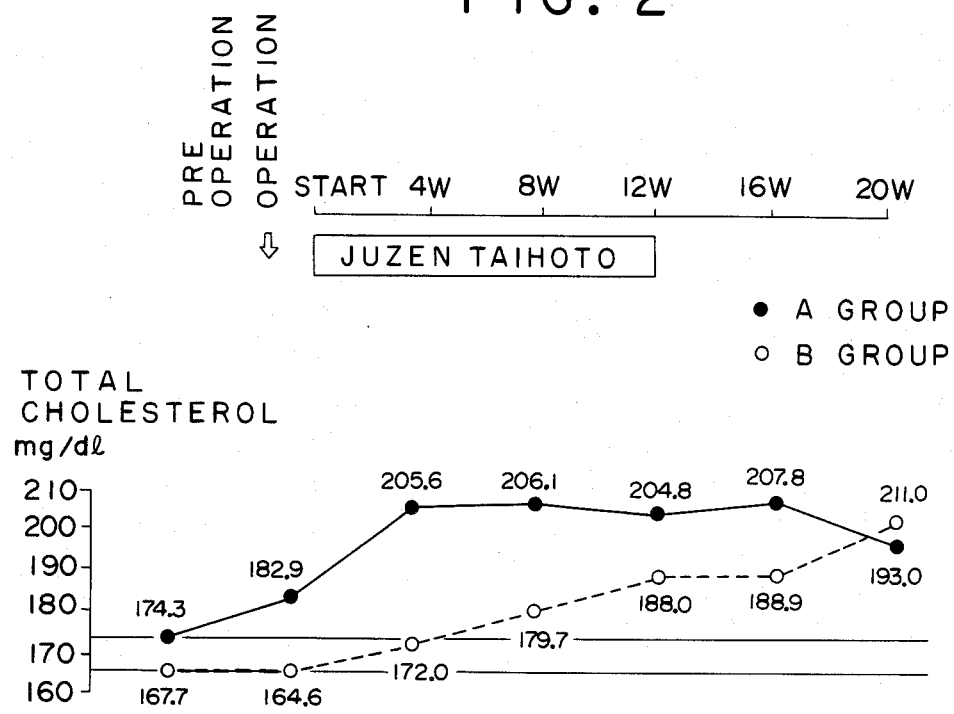

PREPARATION FOR REDUCING CANCER SYMPTOMS WITHOUT TREATING CANCER

This is a continuation-in-part of co-pending application Ser. No. 509,200, filed on June 29, 1983, now abandoned.

BACKGROUND OF THE INVENTION

This invention relates to a drug preparation for reducing cancer symptons without treating cancer. More particularly, the present invention relates to a drug preparation which improves lipid metabolism and eliminates or reduces anorexia in tumor-bearing patients.

Toxohormone L is an acidic protein with a molecular weight of about 70,000 which is isolated from human ascites hepatoma affecting adipose tissue and is a lipid degradation-promoting factor. Toxohormone L causes anorexia on injection into the cerebral ventricle of rats and is thought to be a primary factor in adipose decrease in a body suffering from cancerous cachexia (Cancer Res. 41, 284–288 (1981)).

DESCRIPTION OF THE INVENTION

We have found that an aqueous extract, or an extract with an aqueous solution of a suitable water miscible organic solvent, of one or more crude preparations from the group consisting of Astragali radix, Cinnamomi cortex, Rehmanniae radix, Paeoniae radix, Cnidii rhizoma, Atractylodis lanceae rhizoma, Angelicae radix, Ginseng radix, Hoelen and Glycyrrhizae radix inhibits promotion of adipose degradation and anorexia caused by toxohormone L.

The water or aqueous organic solvent extract of the present invention can be produced by extracting one or more crude preparations from the group consisting of Astragali radix, Cinnamomi cortex, Rehmanniae radix, Paeoniae radix, Cnidii rhizoma, Atractylodis lanceae rhizoma, Angelicae radix, Ginseng radix, Hoelen and Glycyrrhizae radix with water or an aqueous solution comprising 5–50 v/v% of a water miscible organic solvent such as an alcohol (preferably ethanol), filtering the obtained solution and optionally drying by conventional drying means, such as spray-drying, freeze drying or concentration drying.

As used in the specification and claims, the "crude preparations" employed according to the invention are further defined as follows:

Astragali radix (Astragalus root)-Root of *Astragalus membranaceus* Bunge;
Cinnamomi cortex (Cinnamon bark)-Bark (surface thereof optionally omitted) of *Cinnamomum cassia* Blume;
Rehmanniae radix (Rehmannia root)-Root (raw or steamed) of *Rehmannia glutinosa* Liboschitz var. purpurea Makino;
Paenoniae radix (Peony root)-Root of *Paeonia lactiflora* Pallas (*Paeonia albiflora* Pallas var. *trichocarpa* Bunge);
Cnidii rhizoma (Cnidium rhizome)-Rhizome, usually passed through hot water, of *Cnidium officinale* Makino (family Umbelliferae);
Atractylodis lanceae rhizoma (Atractylodes lancea rhizome)-Rhizome of *Atractylodes lancea* De Candolle.
Angelicae radix (Japanese Angelica root)-Root, usually passed through hot water, of *Angelica acutiloba* Kitagawa;
Ginseng radix (Ginseng)-Root (raw or treated by passing through hot water) of *Panax ginseng* C. A. Meyer (*Panax schinseng* Nees) (family Araliacae);
Hoelen (Hoelen)-Sclerotium, outer layer deleted, of *Poria cocos* Wolf (family Polyporaceae);
Glycyrrhizae radix (Glycyrrhiza)-Root and stolon of *Glycyrrhiza glabra* Linne var. glandulifera Regel et Herder, *Glycyrrhiza uralensis* Fischer.

The extract can be obtained by extracting a mixture of one or more of the above crude preparations or by mixing extracts from each crude preparation. Extraction can be carried out at room temperature or with heating; heating at 80°–100° C. is preferred. The extract can be used per se, or prepared in powder, granule, tablet, or capsule form mixed with conventional adjuvants or additives. The extract can optionally be purified by conventional means, such as dialysis and chromatography. The production of the crude extracts is exemplified in the following examples.

EXAMPLE 1

Water (285 ml) was added to 3 g each of Astragali radix, Cinnamomi cortex, Rehmanniae radix, Paeoniae radix, Cnidii rhizoma, Atractylodis lanceae rhizoma, Angelicae radix, Ginseng radix and Hoelen and 1.5 g of Glycyrrhizae radix, and the mixture was heated at 100° C. for 1 hour. The solution was filtered and spray-dried to obtain a dry powdered extract (2.3 g).

EXAMPLE 2

Water (150 ml) was added to Angelicae radix (15 g) and heated at 100° C. for 1 hour. The solution was filtered and dried to obtain a dried extract (1.4 g).

EXAMPLE 3

Angelicae radix in Example 2 was replaced by Astragali radix (15 g) to obtain a dry powered extract (1.8 g).

EXAMPLE 4

Angelicae radix in Example 2 was replaced by Ginseng radix (15 g) to obtain a dry powdered extract (1.7 g).

EXAMPLE 5

Angelicae radix in Example 2 was replaced by Hoelen (15 g) to obtain a dry powered extract (0.6 g).

EXAMPLE 6

Angelicae radix in Example 2 was replaced by Cnidii rhizoma (15 g) to obtain a dry powdered extract (1.4 g).

EXAMPLE 7

Angelicae radix in Example 2 was replaced by Cinnamomi cortex (15 g) to obtain a dry powdered extract (1,8 g).

BRIEF DESCRIPTION OF THE DRAWINGS

With reference to the accompanying drawings,

FIG. 1 shows the effect of a dry preparation of the present invention on anorexia in AH 130 ascites hepatoma-bearing rats compared with a control group;

FIG. 2 shows the total cholesterol levels in clinical patients receiving a preparation according to the invention compared with a control group;

EXPERIMENTAL RESULTS

Figure 3A:
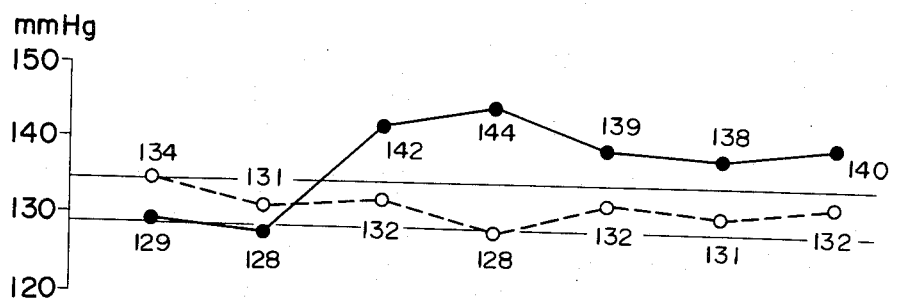
FIGS. 3a and 3b show the blood pressure levels in the patients and in the control group.

The following experimental results show the inhibitory action of the present preparation on the adipose decomposition-promoting activity of toxohormone L.

Adipose tissue slices (100 mg) of the epididymides of male Wister rats, body weight 150-180 g, were suspended in Krebs-Riger carbonate buffer (pH 7.4). Ascites (toxohormone L) collected from hepatitis patients (0.1 ml), the dialysate (0.1 ml) of a supernatant solution obtained by centrifugation of the preparations prepared according to Examples 1-7 dissolved in water (20 mg/ml) and 5% bovine serum albumin (0.5 ml) were combined with 0.1 mM $CaCl_2$ to correct the final volume to 1.0 ml, and the mixture incubated at 37° C. for 2 hours. Liberated fatty acid was then measured by the method of Dole (V. P. Dole, J. Clin. Invest. 35, 150 (1956)).

Table 1 shows the effect of the present extract obtained in Examples 1 to 7 on the adipose decomposition promoting action of toxohormone L compared with a control group. As shown in Table 1, the extract of the present invention inhibits the adipose decomposition-promoting action of toxohormone L.

TABLE 1

|  | Dose (ml) | free fatty acid (Eq/ml R.M.)* | inhibition |
|---|---|---|---|
| Control group administered with extract |  | 4.5 | — |
| Example 1 | 0.1 | 0.0 | 100.0 |
| Example 2 | 0.1 | 2.7 | 40.0 |
| Example 3 | 0.1 | 3.3 | 26.7 |
| Example 4 | 0.1 | 2.9 | 35.6 |
| Example 5 | 0.1 | 1.5 | 66.7 |
| Example 6 | 0.1 | 0.0 | 100.0 |
| Example 7 | 0.1 | 3.6 | 20.0 |

*equivalents/ml of reaction mixture

The following experimental results show that the preparation of the present invention relieves anorexia induced by cancer.

Male, 4 week old Donryu rats were inoculated with AH 130 ascites hepatoma. The rats freely ingested either normal feed (Clea powdered feed) or feed mixed with the preparation obtained according to Example 1 (Clea powdered feed mixed with 100 mg/kg of the preparation of the present invention, designated as drug mixed feed). Feed intakes for the groups given normal feed and drug mixed feed were measured.

FIG. 1 shows the effects of the drug mixed feed on anorexia in rats inoculated with AH 130 ascites hepatoma. As shown in FIG. 1, the preparation of the present invention prevents or reduces anorexias caused by ascites hepatoma.

The acute toxicity of the preparation of the present invention obtained according to the above Examples 1-7 was determined orally for male ddY and male Wister rats. No death was found when the preparations were administered orally at dosages of 15 g/kg, demonstrating the low toxicity and high safety of the present preparations.

Considering the experimental data and the low acute toxicity of the present preparations, an effective dosage for the drug preparation is about 2-10 g per dose, 3 times a day, for adults. The dosage will vary, however, depending on age, body weight and level of disease of the patients.

CLINICAL TRIALS

Cancer patients who had undergone surgical operation were divided into two groups. Group A was administered the preparation of the present invention together with antitumor agent therapy (bleomycin, mitomycin and/or 5-fluorouracil), while group B received antitumor agent chemotherapy only. The patients in this study had been treated for cancer of the esophagus, stomach cancer, and cancer of the colon, among other forms of cancer.

The drug preparation was administered orally in 7.5 g dosages three times a day before meals, for 12 weeks, beginning one or two weeks after operation.

FIG. 2 shows the changes in total cholesterol in the patient's blood. An increase in cholesterol was observed in group A.

Figure 3B:
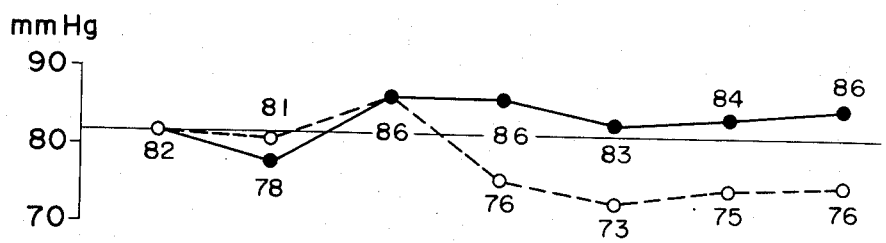

FIG. 3 shows blood pressure changes. An increase in blood pressure was observed in group A.

Figure 4:
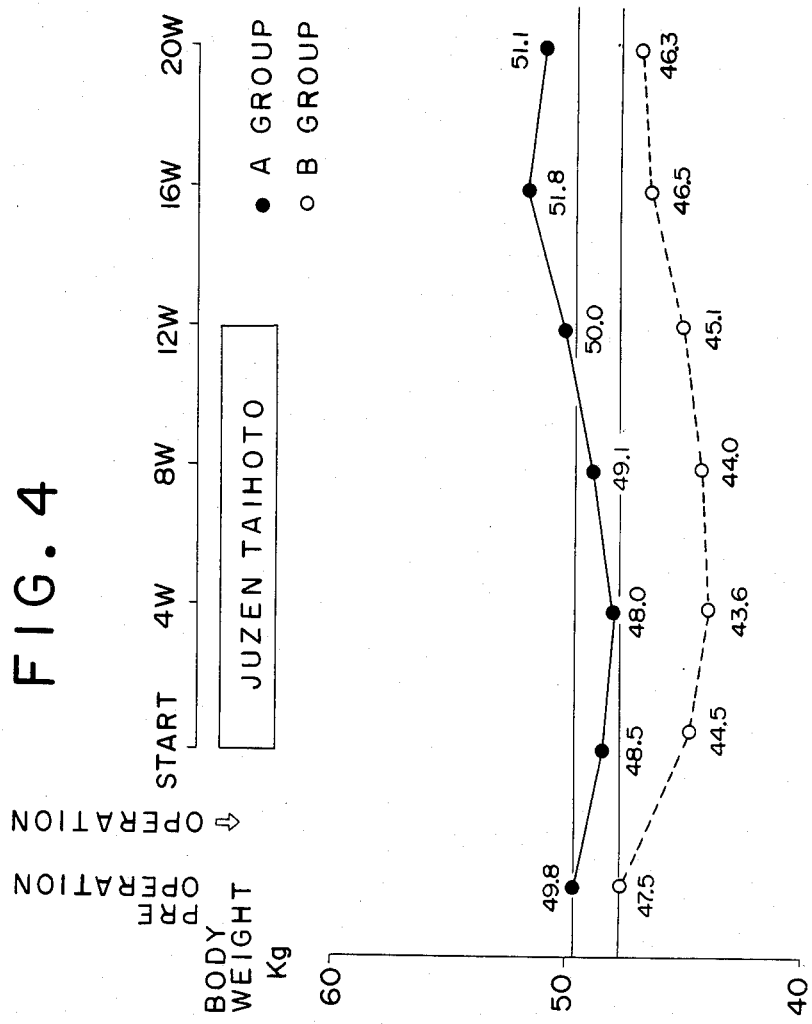
FIG. 4 shows the body weight gain in the patients and control group.

FIG. 4 shows body weight gain. In group B, a slight increase was observed 4 weeks after the operation; however, no recovery was observed after 20 weeks. In group A, body weight recovered to almost preoperation levels after 12 weeks of drug administration.

The following examples further illustrate the present invention but should not be construed as limiting.

EXAMPLE 8

A drug preparation (200 g) obtained according to Examples 1 to 7 was mixed with lactose (89 g) and magnesium stearate (1 g). The mixture was tableted by single tableting machine to produce tablets of 20 mm diameter and about 23 g weight. The tablets were crushed by oscillation and sifted to obtain granules of 20-50 mesh. The granules were taken three times a day in dosages of 3-15 g (corresponding to 2.07-10.34 g of the present extract).

EXAMPLE 9

A drug preparation (200 g) obtained according to Examples 1 to 7 was mixed with fine crystalline cellulose (20 g) and magnesium stearate (5 g). The mixture was tableted by single tableting machine to produce tablets of 7 mm diameter and 225 mg weight. Each tablet contains 20 mg of the drug preparation. The drug is taken 10-50 tablets at a time, three times a day.

EXAMPLE 10

A drug preparation (500 mg) obtained according to Examples 1 to 7 was encapsulated in a hard capsule. The drug is taken 4-20 capsules at a time, three times a day.

We claim:

1. A composition useful in inhibiting promotion of adipose degradation and anorexia, comprising an effective amount to inhibit promotion of adipose degradation and anorexia of an aqueous extract of a mixed crude preparation consisting of two parts by weight of each of Astragali radix, Cinnamomi cortex, Rehmanniae radix, Paeoniae radix, Cnidii rhizoma, Atractylodis lanceae rhizoma, Angelicae radix, Ginseng radix and Hoelen, and one part by weight of Glycyrrhizae radix.

2. A composition according to claim 1, further comprising at least one pharmaceutically acceptable adjuvant or additive.

3. A method for inhibiting promotion of adipose degradation and anorexia in human cancer patients comprising administering an effective amount to inhibit promotion of adipose degradation and anorexia of a composition containing an aqueous extract of a mixed crude preparation consisting of two parts by weight of each of Astragali radix, Cinnamomi cortex, Rehmanniae radix, Paeoniae radix, Cnidii rhizoma, Atractylodis lanceae rhizoma, Angelicae radix, Ginseng radix and Hoelen and one part by weight of Glycyrrhizae radix to said human patients.

4. A method according to claim 3, wherein said composition comprises a dry powdered extract and is administered in 2-10 g does three times daily.

* * * * *